(12) United States Patent
Brillhart et al.

(10) Patent No.: US 6,927,071 B2
(45) Date of Patent: Aug. 9, 2005

(54) METHOD FOR REDUCING NON-SPECIFIC AGGREGATION OF LATEX MICROPARTICLES IN THE PRESENCE OF SERUM OR PLASMA

(75) Inventors: Kurt L. Brillhart, Mission Viejo, CA (US); Julie A. Whiteside, Santa Ana, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 193 days.

(21) Appl. No.: 10/010,005

(22) Filed: Dec. 7, 2001

(65) Prior Publication Data

US 2003/0113794 A1 Jun. 19, 2003

(51) Int. Cl.[7] .................... G01N 33/546; G01N 33/552; G01N 33/553; G01N 33/548
(52) U.S. Cl. ...................... 436/534; 436/525; 436/527; 436/529; 436/530; 436/533; 436/825; 436/826
(58) Field of Search .............................. 436/530, 525, 436/533, 527, 529, 825, 826, 534

(56) References Cited

U.S. PATENT DOCUMENTS

| 4,362,531 A | 12/1982 | de Steenwinkel et al. .. 436/512 |
|---|---|---|
| 4,536,478 A | 8/1985 | Sokoloff et al. ............. 436/533 |
| 4,703,001 A | 10/1987 | Vodian et al. ................. 435/5 |
| 4,847,209 A | 7/1989 | Lewis et al. ................. 436/533 |
| 5,486,479 A | 1/1996 | Ito et al. ...................... 436/533 |
| 5,506,151 A | 4/1996 | Ito et al. ...................... 436/533 |

OTHER PUBLICATIONS

K. Shigenobu et al, Chemical Abstract No. 136: 83390, citing WO 2002/003,068 (Jan. 10, 2002).*

* cited by examiner

*Primary Examiner*—Mary E. Ceperley
(74) *Attorney, Agent, or Firm*—Hogan & Hartson, LLP

(57) ABSTRACT

A particle-enhanced assay for determining an analyte in a test sample in which an additive for reducing non-specific particle aggregation is added in an amount to substantially reduce non-specific aggregation. The additive is selected form the group consisting of triethanolamine, trimethanolamine, N-butyldiethanolamine, 3-dimethylamino-2-methylpropyl chloride, N,N-dimethylglycine, N,N-dimethylguanidine, N,N-dimethylglycine ethyl ester, 3-dimethylaminopropionitrile, and N,N-dietylacetamide.

33 Claims, 1 Drawing Sheet triethanolamine

N,N-dimethylguanidine trimethanolamine

N,N-dimethylglycine ethyl ester

N-butyldiethanolamine 3-dimethylaminopropionitrile 3-dimethylamino-2-methylpropyl chloride N,N-diethylacetamide N,N-dimethylglycine 1-dimethylamino-2-propylamine

METHOD FOR REDUCING NON-SPECIFIC AGGREGATION OF LATEX MICROPARTICLES IN THE PRESENCE OF SERUM OR PLASMA

FIELD OF THE INVENTION

The present invention relates to methods for reducing non-specific aggregation in particle-enhanced assays. More specifically, the methods comprise adding an additive that reduces non-specific aggregation which, when added to an assay reaction mixture, improves the accuracy and reliability of the quantitative or qualitative determination of analyte in a sample by significantly reducing or eliminating non-specific particle aggregation.

BACKGROUND OF THE INVENTION

Immunoassays are assay systems that exploit the ability of an antibody to specifically recognize and bind to a particular analyte or "antigen." An antigen is a substance which is capable of inducing an immune response, i.e., antibody production, when introduced into an animal or human body. The region of a antigen that is recognized by an antibody, and to which the antibody binds, is referred to as an "epitope."

The simplest immunoassay involves merely incubating an antibody that is capable of binding to a target molecule (i.e., the "analyte") with a sample that is suspected to contain the analyte. The presence of the target molecule is determined by the presence, and is proportional to the concentration, of any immune complexes that form through the binding of the antibody and the analyte. In order to facilitate the separation of such immune complexes from the uncomplexed antibody, a solid phase is typically employed. In more sophisticated immunoassays such as particle-enhanced assays, the concentration of the target molecule is determined by binding the antibody to a support such as latex particles, and then incubating the support-bound antibody in the presence of the analyte-containing sample.

Target molecules that have become bound to the immobilized antibody can be detected in any of a variety of ways. For example, the support can be incubated in the presence of a labeled, second antibody (i.e., a "sandwich" immunoassay) that is capable of binding to a second epitope of the target molecule. Immobilization of the labeled antibody on the support thus requires the presence of the target, and is proportional to the concentration of the target in the sample. In an alternative assay, the sample is incubated with a known amount of labeled target and antibody binding site. The presence of any target molecules in the sample competes with the labeled target molecules for the antibody binding sites. Thus, the amount of labeled target molecules that are able to bind the antibody is inversely proportional to the concentration of target molecules in the sample. This is known as a competitive immunoassay.

The various immunoassay formats can be further divided into two main classes, depending upon whether the assay requires the separation of bound species from unbound species. Heterogeneous immunoassays require such purification, and hence entail a separation or isolation step. In contrast, homogeneous assays are designed such that the removal of bound species from unbound species is unnecessary. Because homogeneous assays lack a separation step, and are more easily automated, they are more desirable than heterogeneous assays in applications that entail the screening of large numbers of patients.

In particle-enhanced immunoassays, an immune complex formation caused by a reaction between one or more particle-bound antibodies and the analyte results in particle aggregation. If the immune complex is large enough, it will become capable of scattering light, or of spontaneously precipitating. In such cases, agglutination, nephelometric, or turbidimetric detection methods may be employed. Nephelometric methods measure the light scattered by a suspension of particles or reflected toward a detector that is not in the direct path of light (Stemberg, J. C., *Clin. Chem.* 23: 1456–1464 (1977)). In contrast, turbidimetric methods measure the reduction of light transmitted through the suspension of particles or aggregates. The reduction is caused by reflection, scatter, and absorption of the light by the aggregates. Agglutination assays measure the precipitation of antibody-antigen complexes. Such assays can be extremely sensitive, and are amenable to automation. Because nephelometric and turbidimetric methods do not require the separation of the initially present antibody from the immune complexes formed in the assay, such assays are homogenous immunoassays.

Particle carriers typically used in such agglutination reactions are latex particles (e.g., particles of natural rubber or synthetic rubber latex, polystyrene latex, polyvinyltoluene latex). Polystyrene latex, being a synthetic product, has a longer shelf-life than non-latex carriers. In addition, latex securely binds proteins and other substances, and the antigenic properties of the bound proteins are substantially not impaired. Because of these desirable properties, latex particles have been employed as a raw material for a large variety of serological clinical test reagents.

It has been found, however, that latex particles sensitized with various antigens or antibodies often tend to undergo spontaneous aggregation during storage. In addition, even when a latex is of the type which does not undergo spontaneous aggregation during storage, it sometimes undergoes a non-specific aggregation upon admixture with body fluids such as serum. Non-specific aggregation interferes with the determination of an analyte's presence and/or concentration and can lead to an erroneous diagnosis. As a result, much time and effort has been expended in the search for the means of eliminating non-specific aggregation.

Currently known methods of reducing non-specific interferences in particle-enhanced assays include the following: addition of bovine serum albumin; massive dilution of the test sample up to at least 20-fold; addition of detergents such as are taught in U.S. Pat. No. 4,060,597; rigorous pretreatment of the test sample including heat treatment for 30 minutes at 56° C. as described by Merz et at. (*J. Clin. Micro.*, 5: 596 (1977)) enzymatic treatment with proteases reaction as described by Collet-Cassart et al. (*Clin. Chem.*, 27: 1205, (1981)); treatment with reducing/oxidative reagents as described by Cambiaso et al. (*J. Immuno. Meth.* 28: 13, (1979)); and separation of components using ion exchange chromatography as described in U.S. Pat. No. 4,270,923. However, these methods do not work in all cases. In addition, these methods are time consuming and can carry with them the undesirable effect of drastically reducing the potential sensitivity and accuracy of the immunoassay as a result of the required manipulations.

Another approach to reducing non-specific particle aggregation has been the addition of specific chaotropic or chaotropic-like agents such as those described in U.S. Pat. No. 4,362,531 to de Steenwinkel et al. The described agents, however, include a wide range of dissimilar and unrelated compounds which are effective to varying degrees in relation to one another.

Ito et al. (U.S. Pat. No. 5,506,151) describe urea compounds useful as non-specific reaction suppressors. These urea compounds are hydrolysis products of carbodiimides, and these syntheses require the processing of large amounts of the hazardous and relatively expensive carbodiimide precursor.

For these reasons, the search for additives to aggregation reaction mixtures which reduce or eliminate the effects of non-specific interferences from physiological samples in such immunoassays continues.

SUMMARY OF THE INVENTION

This invention relates to improved particle-enhanced assays for determining the presence and/or concentration of an analyte of interest in a sample. More specifically, the invention relates to a method of reducing non-specific aggregation in particle-enhanced assays by adding to the assay an additive that substantially reduces or eliminates non-specific aggregation.

Accordingly, one aspect of the present invention provides an assay for determining the presence of an analyte of interest in a test sample, comprising:
  (a) forming a reaction mixture by combining:
    (i) a test sample which may contain the analyte of interest;
    (ii) a known amount of sensitized particles having immobilized thereon an analyte-specific binding partner; and
    (iii) a known amount of an additive that reduces non-specific aggregation of said particles, wherein the additive is a compound having the formula:

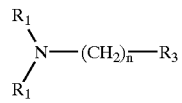

where $R_1$ and $R_2$ independently are substituted or unsubstituted alkyl or $-(CH_2)_m OH$;
m is 1–3;
$R_3$ is hydroxy, cyano, substituted or unsubstituted alkyl, $-COOX$, or $-CH(NH_2)Y$;
X is hydrogen or substituted or unsubstituted alkyl;
Y is hydrogen, substituted or unsubstituted amino, or substituted or unsubstituted alkyl; and
n is 0–3;
  (b) incubating the reaction mixture under conditions that allow said particle-immobilized binding partner to bind to said analyte to cause specific aggregation of said particles, wherein said additive is present in an amount sufficient to reduce non-specific particle aggregation; and
  (c) determining the extent of specific aggregation, wherein the extent is proportional to the amount of said analyte in said sample.

Another aspect of this invention provides an improved indirect assay for determining the presence of an analyte of interest in a sample, comprising adding to the assay an additive that reduces non-specific aggregation, wherein the additive is a compound having the formula:

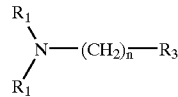

where $R_1$ and $R_2$ independently are substituted or unsubstituted alkyl, or $-(CH_2)_m OH$;
m is 1–3;
$R_3$ is hydroxy, cyano, substituted or unsubstituted alky, $-COOX$, or $-CH(NH_2)Y$;
X is hydrogen or substituted or unsubstituted alkyl;
Y is hydrogen, substituted or unsubstituted amino, or substituted or unsubstituted alkyl; and
n is 0–3.

Another aspect of this invention provides a composition useful in particle-enhanced assays for determining the presence of an analyte of interest in a sample, wherein the composition comprises sensitized particles having immobilized thereon either the analyte of interest or an analyte-specific binding partner, and an additive that reduces non-specific aggregation of the particles, wherein the additive is a compound having the formula:

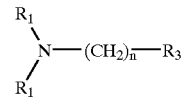

where $R_1$ and $R_2$ independently are substituted or unsubstituted alkyl or $-(CH_2)_m OH$;
m is 1–3;
$R_3$ is hydroxy, cyano, substituted or unsubstituted alkyl, $-COOX$, or $-CH(NH_2)Y$;
X is hydrogen or substituted or unsubstituted alkyl;
Y is hydrogen, substituted or unsubstituted amino, or substituted or unsubstituted alkyl; and
n is 0–3.

A test kit for detecting the presence of an analyte of interest in a test sample is also disclosed. The test kit comprises at least one container that includes an additive for reducing non-specific aggregation of particles in a particle-enhanced assay.

Additional objects, advantages, and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

BRIEF DESCRIPTION OF THE FIGURES

The accompanying drawings, which are incorporated herein and form a part of the specification, illustrate preferred embodiments of the present invention and, together with the description, serve to explain the principles of the invention.

In the Figures.

DETAILED DESCRIPTION OF THE INVENTION

Figure 1:
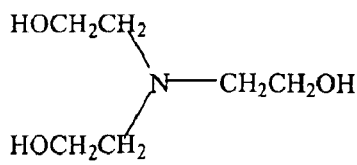
FIG. 1 shows the structures of several additives suitable for use in assays of this invention.
Figure 1:
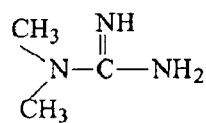
Figure 1:
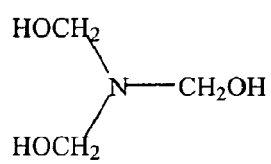
Figure 1:
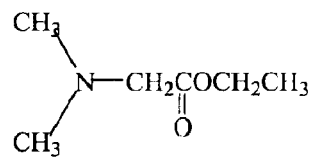
Figure 1:
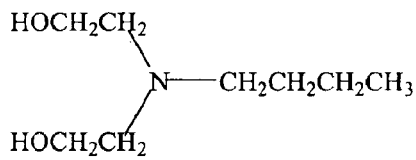
Figure 1:
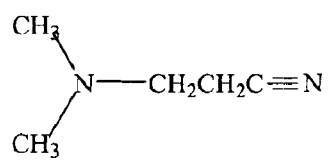
Figure 1:
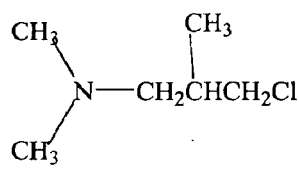
Figure 1:
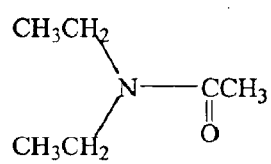
Figure 1:
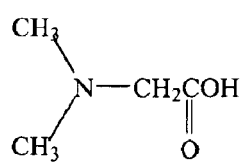
Figure 1:
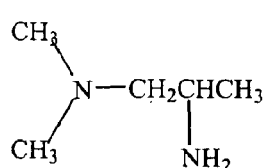

This invention relates to improved particle-enhanced assays for determining the presence of an analyte of interest in a sample. More specifically, the invention provides a method of substantially reducing non-specific aggregation in particle-enhanced assays by adding to the assay an additive that substantially reduces or eliminates non-specific particle aggregation. In one embodiment, the assay comprises the steps of:
  (a) forming a reaction mixture by combining:
    (i) a test sample which may contain the analyte of interest;

(ii) a known amount of sensitized particles having immobilized thereon an analyte-specific binding partner; and (iii) a known amount of an additive that reduces non-specific aggregation of said particles, wherein said additive is a compound having the formula:

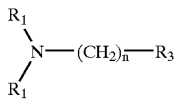

where $R_1$ and $R_2$ independently are substituted or unsubstituted alkyl or $-(CH_2)_m OH$;

m is 1–3;

$R_3$ is hydroxy, cyano, substituted or unsubstituted alkyl, —COOX, or —CH(NH$_2$)Y;

X is hydrogen or substituted or unsubstituted alkyl;

Y is hydrogen, substituted or unsubstituted amino, or substituted or unsubstituted alkyl; and n is 0–3;

(b) incubating the reaction mixture under conditions that allow said particle-immobilized binding partner to bind to said analyte to cause specific aggregation of said particles, wherein said additive is present in an amount sufficient to reduce non-specific particle aggregation; and (c) determining the extent of specific aggregation, wherein the extent is proportional to the amount of said analyte in said sample.

The reaction mixture is formed by combining in an assay medium the test sample, sensitized particles, and an additive that reduces non-specific binding of the particles. As used herein, the terms "sample" or "test sample" are used interchangeably and refer to any sample suspected of containing the analyte of interest. The test sample can be untreated (undiluted), or chemically and/or physically treated, diluted, or concentrated prior to analysis. Examples of samples include, but are not limited to, samples from biological sources such as physiological fluids, including whole blood, plasma, serum, saliva, cerebral spinal fluid, urine, amniotic fluid, urine, feces, mucus, cell or tissue extracts, and any other type of fluid, tissue or material which is suspected of containing an analyte of interest.

As used herein, an "analyte" or "analyte of interest" refers to the substance whose presence and/or concentration in a sample is to be determined. The term "analyte" includes any substance for which there exists a specific binding partner (e.g., a binding molecule or substance which specifically binds the analyte), or for which a specific binding partner can be prepared. Representative analytes include, but are not limited to, drugs, antigens, haptens, antibodies, proteins, peptides, amino acids, hormones, steroids, cancer cell markers, tissue cells, viruses, vitamins, nucleic acids, and pesticides.

The term "antibody" as used herein refers to immunoglobulins that are produced in response to the detection of a foreign substance, and includes intact molecules as well as functional fragments thereof, such as Fab, F(ab')$_2$, and Fv.

To conduct the assays of the present invention, it is necessary to provide sensitized particles comprising insoluble particles coated with an analyte-specific binding partner or the analyte of interest. The insoluble particles may be any natural or synthetic material capable of having a binding molecule or analyte of interest disposed thereon. Such materials include latex polymeric materials, e.g., polymers of olefinically unsaturated monomers such as polystyrene, acrylonitrile and polybutadiene, and derivatives and copolymers thereof (see, e.g., Bangs, L. B., Uniform Latex Particles, Seragen, Ind., 1984 and U.S. Pat. No. 4,305,925), glass, acrylamide or methacrylate, nylon, microscopic oxide powders, dextrans, cellulose and derivatives thereof. The invention is particularly directed to the embodiments of such assays wherein the particles are latex particles, such as carboxylate modified latex particles.

Methods of preparing sensitized particles are well known to those skilled in the art. The term "sensitized particles" refers to an insoluble particle having one or more layers of an analyte-specific binding partner or an analyte of interest immobilized thereon. The term "immobilized" refers to attachment of the binding partner or the analyte to the particle by covalent (chemical) or non-covalent (e.g., physical adsorption) bonds.

The attachment of the binding partner or the analyte to the insoluble particles is a matter of applying conventional techniques. In general, the binding partner or the analyte may be disposed on the particles in accordance with standard techniques, such as physical (passive) absorption, facilitated (forced) absorption and covalent coupling methodologies. U.S. Pat. No. 4,181,636, which is specifically incorporated herein by reference, teaches carboxylated latex polymers coupled to immunologically active materials through a water soluble activating agent. U.S. Pat. No. 4,264,766, which is specifically incorporated herein by reference, is directed to latex polymers having active groups such as carboxyl and amino groups to which water soluble polyhydroxy compounds can be covalently attached, and which upon treatment with an activating agent, e.g., carbodiimide, may be covalently coupled to an immunologically active agent. See also U.S. Pat. Nos. 4,521,521 and 4,305,925, which are specifically incorporated herein by reference. The techniques disclosed in these patents or other techniques well known to those skilled in the art may be used to attach the binding partners or analytes to the particles.

In direct assays of this invention, the sensitized particle comprise insoluble particles having an analyte-specific binding partner immobilized thereon. As used herein, the term "binding partner" refers to a molecule or substance that recognizes and binds to the analyte of interest, and exhibits negligible cross-reactivity with other molecules or substances. Typical binding molecules include, but are not limited to, antigens, antigen fragments, receptors, nucleic acids, and polyclonal antibodies, monoclonal antibodies, and antibody fragments. Such binding molecules specific for a given analyte may be obtained from commercial sources or may be prepared in accordance with standard procedures known to those skilled in the art. Examples of analyte:specific binding partner pairs include, but are not limited to, hapten:antibody, biotin:avidin, hormone:receptor, polypeptide:antibody, and oligonucleotide:complementary DNA or RNA.

In indirect assays of this invention, the sensitized particles comprise insoluble particles having the analyte of interest immobilized thereon.

Forming the reaction mixture in assays according to this invention further includes the addition of one or more additives in an amount sufficient to substantially reduce or eliminate non-specific aggregation of the sensitized particles. As discussed above, in addition to undergoing specific aggregation reactions (complex formation) between the analyte and binding partner, the particles in particle-enhanced assays also undergo non-specific aggregation. For purposes of this invention, the terms "specific aggregation" and "complex formation" are used interchangeably and refer to the specific recognition and binding between the analyte of interest and the analyte-specific binding partner, one of which is immobilized on an insoluble particle. These terms include the binding of one analyte to one binding partner, and the process wherein two or more sensitized particles are linked together by the analyte to produce aggregates of particles, such as dimers, trimers, and higher order networks of aggregated particles.

In contrast, the term "non-specific binding" as used herein refers generally to any binding which is not caused by specific binding, and more specifically to the aggregation of sensitized particles by means other than the linking of two or more particles by the analyte. Non-specific binding may result from several factors, including immune complexing agents, charged proteins, and antibody-interfering proteins which may be present in the assay reaction mixture.

Suitable additives for use in the assays of the invention include compounds having the formula:

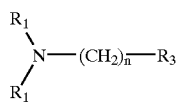

where $R_1$ and $R_2$ independently are substituted or unsubstituted alkyl or $-(CH_2)_m OH$;
m is 1–3;
$R_3$ is hydroxy, cyano, substituted or unsubstituted alkyl, $-COOX$, or $-CH(NH_2)Y$,
X is hydrogen or substituted or unsubstituted alkyl;
Y is hydrogen, substituted or unsubstituted amino, or substituted or unsubstituted alkyl; and
n is 0–3.

As used herein, "alkyl" refers to groups having from one to six carbons and may be straight chain or branched alkyl groups having one or more substituents. The substituents of the substituted alkyl groups include, for example, hydroxy, nitro, amino, and keto, lower alkoxy groups such as methoxy, ethoxy, butoxy, and halogens such as chloro, fluoro, bromo and iodo. Examples of additives suitable for purposes of this invention include those illustrated in FIG. 1. In one embodiment, the additive is 3-dimethylamino-2-methylpropylchloride (Acros or Fischer Scientific). In another embodiment, the additive is N,N-dimethylglycine ethyl ester (Fluka-Chemika-Biochem).

The additives for reducing non-specific aggregation disclosed herein are generally commercially available compounds or are prepared by simple organic reactions well known to those of ordinary skill in the art. In addition, the additives do not require further processing in order to be effective. That is, the additives can be used directly as obtained from the manufacturer or as isolated from a reaction mixture for preparing the additive. Therefore, the possibility of inadvertently using a partially treated additive in the assays of this invention is prevented.

For purposes of this invention, an amount of an additive disclosed herein sufficient to substantially reduce non-specific aggregation in particle-enhanced assays is between about 0.02M and 0.2M, preferably between about 0.35M and 0.125M, based on the total assay solution volume. According to this invention, non-specific aggregation is substantially reduced when a significant number of patient samples of known concentration are assayed and recover ±10% of target, or when a significant number of true negative samples, containing no antigen, are assayed and none cause aggregation to occur. Aggregation should only occur in the presence of the antigen.

The reaction mixture components may be added in any order. In one embodiment, the additive for reducing non-specific aggregation is first incubated with the sample, and then the sensitized particles are added to the resultant mixture.

In the incubation step for a direct assay, the reaction mixture comprising the test sample, the sensitized particles and the additive are incubated under conditions that allow binding between the analyte in the sample and the immobilized binding partners. The general methods of the in vitro assay of analytes in fluid samples by particle-enhanced procedures are well known in the art and need not be described in detail here. The binding between the analyte and the sensitized particles results in specific aggregation of the particles which can be detected, thereby indicating the presence of the analyte. The specific aggregation can be measured and correlated with the amount of analyte in the sample. The presence of an additive described herein in the reaction mixture significantly reduces non-specific particle aggregation, thereby improving the accuracy of this measurement.

In another embodiment of this invention, the assay of this invention is an indirect assay. An indirect assay involves combining the test sample which may contain the analyte of interest with sensitized particles having the analyte of interest immobilized thereon along with an analyte-specific binding partner and an additive that reduces non-specific aggregation to form a reaction mixture. The reaction mixture is incubated under conditions that allow binding between the binding partner and the analyte in the sample or the particle-immobilized analyte. In a competitive assay, specific particle aggregation occurs to an extent dependent on the amount of analyte present in the sample. That is, the analyte present in the sample will compete with the particle-immobilized analyte for the binding partner. An increase in the binding of the analyte in the sample with the binding partner results in a decrease in the binding of the immobilized analyte with the binding partner. This in turn reduces specific particle aggregation, resulting in a decrease in turbidity. Thus, the presence and/or concentration of analyte in a sample can be determined by detecting a change in turbidity of the reaction mixture. In competitive immunoassays, the extent of aggregation is inversely proportional to the amount of analyte present in the test sample. The presence of an additive described herein in the reaction mixture significantly reduces non-specific particle aggregation, thereby improving the accuracy of the measurement of analyte concentration.

The additives disclosed herein are useful for improving the accuracy and reliability of the assay of analytes in any particle-enhanced assay by significantly reducing non-specific particle aggregation. In particular, homogenous, turbidimetric, and nephelometric assays such as latex agglutination tests (including direct and competitive homogenous particle-enhanced assays), can be improved through the use of the additives described herein.

The methods of this invention improve the correlation of the assay results to heterogeneous reference methods. That is, different samples produce differing degrees of non-specific aggregation. Therefore, only partial aggregation of the sensitized particles can occur, which would add to the specific aggregation. This results in a recovered value that is either slightly elevated or depressed compared to its true value. In a heterogeneous assay, interferents are removed during the assay before the binding partner is added to the reaction mixture, thus recovering the analyte's true concentration. An interferent is any substance found in the sample to be assayed that either prevents or participates in the reaction between the antibody and the antigen, but is autonomous to the reaction. In the homogeneous methods of this invention, the additives prevent non-specific aggregation, thus removing any partial aggregation and allowing only specific aggregation to occur. This results in the recovery of the true concentration of the analyte of interest, and therefore better correlation between homogeneous and heterogeneous assays.

In detection of specific aggregation in the assays of this invention, the presence of the analyte in the test sample an be determined visually or with the use of an appropriate instrument. Typically, aggregation is measured using conventional procedures such as turbidimetry, nephelometry, conventional light scattering techniques, quasi-elastic scattering methods, angular anisotropic scattering determination, and other methods well known to those skilled in the art. The resulting signal given by the aggregated particles is then detected, measured, and correlated to the amount of analyte in the test sample. Aggregation results in increased turbidity in the reaction mixture. In the presence of the analyte, specific aggregation in a direct assay is directly proportional to the amount of analyte in the sample, whereas in a competitive assay the extent of specific aggregation is inversely proportional to the amount of analyte present in the test sample. Such measurements are well known to those skilled in the art. The amount of analyte present can be determined by using standard curves (or other standard results). This technique is well known by those skilled in the art and need not be described further.

Formulations for use in assays to detect an analyte of interest can be assembled as test kits of at least one or more containers. These test kits can provide a convenient assortment of assay components which can be partially or completely pre-combined or uncombined.

In one embodiment, a kit according to the present invention for use in a direct assay comprises first and second container means, the first container means containing insoluble particles sensitized with an analyte-specific binding partner, the second container means containing at least one of the above-described additives for reducing non-specific aggregation of the particles in an amount that reduces non-specific aggregation of particles. Alternatively, the sensitized particles and the additive can be contained in the same container.

In another embodiment, a kit according to the present invention for use in a competitive assay comprises first, second and third container means, the first container means containing insoluble particles sensitized with the analyte of interest, the second container means containing an analyte-specific binding partner, and the third container means containing at least one of the above-described additives for reducing non-specific aggregation of the particles in an amount that reduces non-specific aggregation of particles. Alternatively, one of the containers contains a composition comprising a mixture of the sensitized particles and an additive disclosed herein for reducing non-specific aggregation.

The methods of this invention including the above-described additives offer several advantages over conventional methods for reducing non-specific aggregation. First, the additives are effective at low concentrations. For example, additive concentrations as low as 0.2M are effective in substantially reducing non-specific aggregation.

In addition, unlike additives known in the prior art, the additives disclosed herein are inexpensive, and do not require further processing in order to be effective. Therefore, the possibility of inadvertently using a partially treated additive is eliminated. This is an improvement over the use of other additives such as urea additives described in U.S. Pat. No. 5,506,151 to Ito et al., since the synthesis of the ureas of Ito et al. requires processing large amounts of the hazardous and relatively expensive carbodiimide precursor.

Having now generally described the invention, the same will be more readily understood through reference to the following examples which are provided by way of illustration, and are not intended to be limiting of the present invention.

EXAMPLE

The ten different compounds shown in FIG. 1 were added individually at concentrations of 50 mM to a reaction buffer, which was previously formulated to yield the best responses under ideal patient matrix conditions. Specifically, the ten compounds tested were triethanolamine (TES), trimethanolamine (TME), N-butyldiethanolamine (N,N-BUTY), 3-dimethylamino-2-methylpropyl chloride (3-D-2-MOL), N,N-dimethylglycine (DMG), N,N-dimethylguanidine (DGD), N,N-dimethylglycine ethyl ester (DMEE), 3-dimethylaminopropionitrile (DMPN), N,N-dietylacetamide (N,N-DEAA), and 1-dimethylamino-2-propylamine (1-D-2-PA). A control comprising the base reaction buffer with no additive was also assayed. A dose response curve was assayed to determine the effect of each additive on specific aggregation in the presence of antibody (digoxin) against increasing amounts of antigen (a digoxin drug). The resulting aggregation number at each concentration for each buffer containing one of the ten additives shown in FIG. 1 is represented Table 1. A sample which causes non-specific aggregation would produce an aggregation number between the first and the last number of the specific dose response represented in Table 1.

Eight patient samples previously identified as known non-specific aggregators of digoxin-coated latex particles were assayed with each of ten additives shown in FIG. 1 in the absence of antibody. A control comprising the base reaction buffer with no additive was also assayed. The resulting aggregation number for each patient for each buffer containing one of ten additives is represented in Table 2. A control consisting of the base reaction buffer with no additive was also assayed.

As shown in Table 2, five of the ten compounds tested, i.e., TEA, TMA, 3-D-2-MOL, DMG, and DMEE, were shown to reduce the incidence of non-specific aggregation of the reaction buffer. With the exception of sample No. 8 having N,N-dimethylglycine (DMG) as the additive, all previous aggregators produced rates lower than the 4.5 ng/mL standard with the additives. Of the remaining five compounds, three significantly reduced the level of non-specific aggregation and may be more effective at higher concentrations. N,N-Dimethylguanidine (DGD) and N,N-butyldiethanolamine (N,N-BUTY) were the least effective at reducing non-specific aggregation.

The two compounds which reduced non-specific aggregation the most were 3-dimethylamino-2-methylproypyl chloride (3-D-3-MCL) and N,N-dimethylglycine ethyl ester (DMEE). Thus, a second experiment was performed with 3-D-3-MCL and DMEE at concentrations of 0.05M added separately to the reaction buffer (following the procedures for the experiment summarized in Table 1). This experiment tested the specific response as well as the non-specific response. Both buffers were successfully calibrated in the presence of antibody using standards of increasing digoxin concentration from 0 to 4.5 ng/mL. The success of the calibration was verified through the use of known controls whose levels are spaced throughout the measuring range. Samples from one hundred patients with elevated concentrations of Rumatoid Factor (known by the industry for causing non-specific aggregation) were assayed in the absence of antibody. If a sample causes non-specific aggregation then it will recover a concentration within the measuring range of 0 to 4.5 ng/mL even in the absence of antibody. The lower the recovered concentration, the higher the rate of non-specific aggregation. For both 3-D-3-MCL and DMEE, zero out of 100 patients yielded a concentration within the measuring range of 0 to 4.5 ng/mL, and all patients reported out of range high. Both 3-D-3-MCL and DMEE protected the digoxin-coated latex particles from aggregating non-specifically in these samples without interference to the specific aggregation.

experimentation. The scope of the invention is, therefore, indicated by the appended claims rather than by the foregoing description. All changes that come within the meaning and range of the equivalence of the claims are to be embraced within their scope.

We claim:

1. An assay for detecting the presence of an analyte of interest in a test sample, comprising:
   (a) forming a reaction mixture by combining:
      (i) said test sample;
      (ii) a known amount of sensitized particles having immobilized thereon an analyte-specific binding partner; and
      (iii) a known amount of an additive that reduces non-specific aggregation of said particles, wherein

TABLE 1

Specific Aggregation in reaction buffer

| SAMPLE CONC. (ng/mL) | CONTROL | TEA | TMA | N,N-BUTY | 3-D-2-MOL | DMG | DGD | DMEE | DMPN | N,N-DEAA | 1-D-2-PA |
|---|---|---|---|---|---|---|---|---|---|---|---|
| 0.0 | 13.4 | 11.5 | 11.2 | 11.5 | 11.4 | 11.4 | 12.1 | 11.6 | 11.1 | 11.4 | 11.1 |
| 0.5 | 11.2 | 9.5 | 9.4 | 9.8 | 9.7 | 9.6 | 10.4 | 9.7 | 9.4 | 9.7 | 9.9 |
| 1.0 | 9.1 | 7.6 | — | — | — | — | | | — | 8.3 | 7.7 |
| 2.0 | 6.4 | 5.2 | — | — | — | — | | | — | 5.9 | 5.5 |
| 3.0 | 4.3 | 3.3 | 3.8 | 3.8 | 4.0 | 3.6 | 3.8 | 4.4 | 3.8 | 4.3 | 3.5 |
| 4.5 | 1.8 | 1.6 | 2.0 | 1.9 | 2.3 | 1.7 | 2.0 | 2.5 | 2.1 | 2.5 | 1.8 |

TEA: triethanolamine
DGD: N,N-dimethylguanidine
TMA: trimethanolamine
DMEE: N,N-dimethylglycine ethyl ester
N,N-BUTY: N,N-butyldiethanolamine
DMPN: N,N-dimethylaminopropionitrite
3-D-2-MOL: 3-dimethylamino-2-methylpropyl
N,N-DEAA: N,N-diethylacetamide chloride
1-D-2-PA: 1-dimethylamino-2-propylamine
DMG: N,N-dimethylglycine

TABLE 2

Non-Specific Aggregation

| SAMPLE NO. | CONTROL | TEA | TMA | N,N-BUTY | 3-D-2-MOL | DMG | DGD | DMEE | DMPN | N,N-DEAA | 1-D-2-PA |
|---|---|---|---|---|---|---|---|---|---|---|---|
| 1 | 1.8 | — | — | 2.1 | 1.5 | 0.3 | 1.4 | 0.3 | 0.7 | — | — |
| 2 | 2.8 | — | 0.6 | 2.8 | 0.8 | 0.4 | 2.7 | 0.5 | 0.7 | 2.1 | 1.1 |
| 3 | 1.9 | 0.5 | 0.8 | 1.8 | 0.8 | — | — | — | 0.6 | — | — |
| 4 | 2.6 | 1.1 | 1.0 | 2.8 | 0.9 | 0.5 | 2.7 | 0.9 | 0.7 | 2.1 | 1.1 |
| 5 | 5.7 | 1.0 | 0.8 | — | — | — | — | — | — | — | — |
| 6 | 2.9 | 0.7 | — | — | — | — | — | — | — | — | — |
| 7 | 4.1 | — | 0.6 | 3.1 | 0.8 | 0.4 | 2.0 | 0.4 | 0.6 | 1.9 | 0.4 |
| 8 | 10.6 | — | 0.9 | — | 0.9 | 1.9 | 9.1 | 1.2 | 2.9 | 8.3 | 3.9 |

TEA: triethanolamine
DGD: N,N-dimethylguanidine
TMA: trimethanolamine
DMEE: N,N-dimethylglycine ethyl ester
N,N-BUTY: N,N-butyldiethanolamine
DMPN: N,N-dimethylaminopropionitrile
3-D-2-MOL: 3-dimethylamino-2-methylpropyl
N,N-DEAA: N,N-diethylacetamide chloride
1-D-2-PA: 1-dimethylamino-2-propylamine
DMG: N,N-dimethylglycine The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue said additive comprises a compound selected from the group consisting of triethanolamine, trimethanolamine, N-butyldiethanolamine, 3-dimethylamino-2-methylpropyl chloride, N,N-dimethylglycine, N,N-dimethylguanidine, N,N-dimethylglycine ethyl ester, 3-dimethylaminopropionitrile, and N,N-diethylacetamide;

(b) incubating the reaction mixture under conditions that allow said particle-immobilized binding partner to bind to said analyte to cause specific aggregation of said particles, wherein said additive is present in an amount sufficient to reduce non-specific particle aggregation; and (c) determining the extent of specific aggregation, wherein the extent is proportional to the amount of said analyte in said sample.

2. The assay of claim 1, wherein said additive is present in a concentration ranging from about 0.02 M to 0.2 M based on the total volume of the reaction mixture.

3. The assay of claim 1, wherein said additive is N,N-dimethylglycine ethyl ester.

4. The assay of claim 1, wherein said additive is 3-dimethylamino-2-methylpropyl chloride.

5. The assay of claim 1, wherein said particles comprise latex particles.

6. The assay of claim 1, wherein said test sample is selected from the group consisting of whole blood, plasma, serum, saliva, cerebral spinal fluid, urine, amniotic fluid, urine, feces, mucus, cell extracts, and tissue extracts.

7. The assay of claim 1, wherein said analyte is selected from the group consisting of drugs, antigens, haptens, antibodies, proteins, peptides, amino acids, hormones, steroids, cancer cell markers, tissue cells, viruses, vitamins, nucleic acids, and pesticides.

8. The assay of claim 1, wherein said binding partner is selected from the group consisting of antigens, antigen fragments, receptors, nucleic acids, and polyclonal antibodies, monoclonal antibodies, and antibody fragments.

9. An indirect assay for determining the presence of an analyte of interest in a test sample, comprising:

(a) providing a sample which may contain the analyte of interest;

(b) providing a known amount of a suspension of sensitized particles having analyte of interest immobilized thereon;

(c) providing a known amount of an analyte-specific binding partner;

(d) providing an additive that reduces non-specific aggregation of said particles, wherein said additive comprises a compound selected from the group consisting of triethanolamine, trimethanolamine, N-butyldiethanolamine, 3-dimethylamino-2-methylpropyl chloride, N,N-dimethylglycine, N,N-dimethylguanidine, N,N-dimethylglycine ethyl ester, 3-dimethylaminopropionitrile, and N,N-diethylacetamide;

(e) combining said sample with said sensitized particles, said binding partner and said additive under conditions that allow binding between said binding partner and said particle-immobilized analyte to cause specific aggregation of said particles or to said analyte in said sample, wherein said additive is present in an amount sufficient to reduce non-specific particle aggregation; and (f) determining the amount of said particle-immobilized analyte that is bound with said binding partner, wherein the amount is inversely proportional to the amount of said analyte in said sample.

10. The assay of claim 9, wherein said additive is present in a concentration ranging from about 0.02M to 0.2M based on the total volume of the reaction mixture.

11. The assay of claim 9, wherein said additive is N,N-dimethylglycine ethyl ester.

12. The assay of claim 9, wherein said additive is 3-dimethylamino-2-methylpropyl chloride.

13. The assay of claim 9, wherein said particles comprise latex particles.

14. The assay of claim 9, wherein said test sample is selected from the group consisting of whole blood, plasma, serum, saliva, cerebral spinal fluid, urine, amniotic fluid, urine, feces, mucus, cell extracts, and tissue extracts.

15. The assay of claim 9, wherein step (e) further comprises first mixing said test sample with said binding partner and said additive, and combining the resultant mixture with said sensitized particles.

16. The assay of claim 9, wherein step (e) further comprises first mixing said test sample with said sensitized particles and said additive, and combining the resultant mixture with said binding partner.

17. The assay of claim 9, wherein said analyte is selected from the group consisting of drugs, antigens, haptens, antibodies, proteins, peptides, amino acids, hormones, steroids, cancer cell markers, tissue cells, viruses, vitamins, nucleic acids, and pesticides.

18. The assay of claim 9, wherein said binding partner is selected from the group consisting of antigens, antigen fragments, receptors, nucleic acids, and polyclonal antibodies, monoclonal antibodies, and antibody fragments.

19. A kit for assaying an analyte in a test sample, said kit comprising first and second container means, said first container means containing sensitized particles having an analyte-specific binding partner immobilized thereon, said second container means containing a sufficient amount of an additive to reduce non-specific aggregation of said particles, wherein said additive comprises a compound selected from the group consisting of triethanolamine, trimethanolamine, N-butyldiethanolamine, 3-dimethylamino-2-methylpropyl chloride, N,N-dimethylglycine, N,N-dimethylguanidine, N,N-dimethylglycine ethyl ester, 3-dimethylaminopropionitrile, and N,N-diethylacetamide.

20. The kit of claim 19, wherein said additive is N,N-dimethylglycine ethyl ester.

21. The kit of claim 19, wherein said additive is 3-dimethylamino-2-methylpropyl chloride.

22. The kit of claim 19, wherein said additive is present in a concentration ranging from about 0.02M to 0.2M based on the total volume of the reaction mixture.

23. The kit of claim 19, wherein said test sample is selected from the group consisting of whole blood, plasma, serum, saliva, cerebral spinal fluid, urine, amniotic fluid, urine, feces, mucus, cell extracts and tissue extracts.

24. The kit of claim 19, wherein said analyte is selected from the group consisting of drugs, antigens, haptens, antibodies, proteins, peptides, amino acids, hormones, steroids, cancer cell markers, tissue cells, viruses, vitamins, nucleic acids, and pesticides.

25. The kit of claim 19, wherein said binding partner is selected from the group consisting of antigens, antigen fragments, receptors, nucleic acids, and polyclonal antibodies, monoclonal antibodies, and antibody fragments.

26. The kit of claim 19, wherein said particles are latex particles.

27. A composition useful for assaying an analyte of interest, said composition comprising microparticles having an analyte-specific binding partner immobilized thereon, and a sufficient amount of an additive to reduce non-specific aggregation of said particles, wherein said additive comprises a compound selected from the group consisting of triethanolamine, trimethanolamine, N-butyldiethanolamine, 3-dimethylamino-2-methylpropyl chloride, N,N-dimethylglycine, N,N-dimethylguanidine, N,N-dimethylglycine ethyl ester, 3-dimethylaminopropionitrile, and N,N-diethylacetamide.

28. The composition of claim 27, wherein said additive is N,N-dimethylglycine ethyl ester.

29. The composition of claim 27, wherein said additive is 3-dimethylamino-2-methylpropyl chloride.

30. The composition of claim 27, wherein said particles are latex particles.

31. The composition of claim 27, wherein said analyte is selected from the group consisting of drugs, antigens, haptens, antibodies, proteins, peptides, amino acids, hormones, steroids, cancer cell markers, tissue cells, viruses, vitamins, nucleic acids, and pesticides.

32. The composition of claim 27, wherein said binding partner is selected from the group consisting of antigens, antigen fragments, receptors, nucleic acids, and polyclonal antibodies, monoclonal antibodies, and antibody fragments.

33. The composition of claim 27, wherein said additive is present in a concentration ranging from about 0.02M to 0.2M.

* * * * *